US012589209B2

(12) United States Patent
Schwartzentruber

(10) Patent No.: US 12,589,209 B2
(45) Date of Patent: Mar. 31, 2026

(54) SYSTEM WITH A MONITORING DEVICE

(71) Applicant: QUIO TECHNOLOGIES LLC, New York, NY (US)

(72) Inventor: Jared Schwartzentruber, New York, NY (US)

(73) Assignee: SHL Medical AG, Zug (CH)

( * ) Notice: Subject to any disclaimer, the term of this patent is extended or adjusted under 35 U.S.C. 154(b) by 913 days.

(21) Appl. No.: 17/621,332

(22) PCT Filed: Jun. 23, 2020

(86) PCT No.: PCT/IB2020/055905
§ 371 (c)(1),
(2) Date: Dec. 21, 2021

(87) PCT Pub. No.: WO2020/261106
PCT Pub. Date: Dec. 30, 2020

(65) Prior Publication Data
US 2022/0355041 A1     Nov. 10, 2022

Related U.S. Application Data

(60) Provisional application No. 62/866,582, filed on Jun. 25, 2019.

(30) Foreign Application Priority Data

Oct. 7, 2019     (EP) .................................... 19201666

(51) Int. Cl.
A61M 5/315         (2006.01)
A61M 5/20          (2006.01)

(52) U.S. Cl.
CPC ...... A61M 5/31568 (2013.01); A61M 5/2033 (2013.01); *A61M 2005/206* (2013.01);
(Continued)

(58) Field of Classification Search
CPC .. A61M 2205/3379; A61M 2205/3317; A61M 2205/3327; A61M 2205/023333;
(Continued)

(56) References Cited

U.S. PATENT DOCUMENTS

| 10,702,658 B2 * | 7/2020 | Shekalim | .......... A61M 5/31525 |
| 11,197,963 B2 * | 12/2021 | Helmer | .................. A61M 5/20 |

(Continued)

FOREIGN PATENT DOCUMENTS

| EP | 2781230 A1 * | 9/2014 | ............. A61M 5/24 |
| WO | 02/064196 A1 | 8/2002 | |

(Continued)

OTHER PUBLICATIONS

EP 2 781 230 A1 (Year: 2013).*
International Search Report and Written Opinion for Int. App. No. PCT/IB2020/055905, mailed Aug. 19, 2020.

*Primary Examiner* — Cris L. Rodriguez
(74) *Attorney, Agent, or Firm* — McDonnell Boehnen Hulbert & Berghoff LLP

(57)                ABSTRACT

A system is presented including a monitoring device and a medicament delivery device, where the monitoring device is configured to be releasably connected to the medicament delivery device and wherein the monitoring device comprises an induction sensor configured to detect a state of an electrically conductive drive member of the medicament delivery device in an medicament delivery process through an electrical current which is generated by a magnet field by the induction sensor on the electrically conductive drive element.

14 Claims, 3 Drawing Sheets

(52) U.S. Cl.
CPC .............. *A61M 2205/3317* (2013.01); *A61M 2205/3375* (2013.01); *A61M 2205/3576* (2013.01); *A61M 2205/50* (2013.01)

(58) Field of Classification Search
CPC .. A61M 5/31576; A61M 5/2422; A61M 5/24; A61M 2205/2006; A61M 5/31568; A61M 5/2033; A61M 2005/2006; A61M 5/20; A61M 2005/206; A61M 2205/3375; A61M 2205/3576; A61M 2205/3584; A61M 2205/3592; A61M 2205/50; A61M 2205/8206
See application file for complete search history.

(56) References Cited

U.S. PATENT DOCUMENTS

| | | | | |
|---|---|---|---|---|
| 2006/0111666 A1* | 5/2006 | Hommann | .......... | A61M 5/2066 604/134 |
| 2011/0009821 A1* | 1/2011 | Jespersen | ............ | A61M 5/1452 604/131 |
| 2016/0175527 A1* | 6/2016 | Mccullough | ...... | A61M 5/31501 |
| 2017/0124284 A1* | 5/2017 | McCullough | ..... | A61M 5/31568 |
| 2018/0200451 A1* | 7/2018 | Shekalim | .............. | G01F 11/029 |
| 2019/0217022 A1* | 7/2019 | Gentz | .................... | A61M 5/20 |
| 2020/0324055 A1* | 10/2020 | Schabbach | .......... | A61M 5/3155 |
| 2020/0405964 A1* | 12/2020 | Faught | ................... | G09F 3/208 |

FOREIGN PATENT DOCUMENTS

| | | | | |
|---|---|---|---|---|
| WO | WO-2014064691 A2 * | 5/2014 | ........ | A61M 5/31535 |
| WO | 2016/142216 A1 | 9/2016 | | |
| WO | 2017/050781 A1 | 3/2017 | | |
| WO | WO-2018064784 A1 * | 4/2018 | ............. | A61M 5/20 |
| WO | WO-2019121608 A1 * | 6/2019 | ........ | A61M 5/31546 |
| WO | WO-2019121612 A1 * | 6/2019 | ............ | A61M 5/178 |

* cited by examiner

SYSTEM WITH A MONITORING DEVICE

CROSS REFERENCE TO RELATED APPLICATIONS

The present application is a U.S. National Phase Application pursuant to 35 U.S.C. § 371 of International Application No. PCT/IB2020/055905 filed Jun. 23, 2020, which claims priority to U.S. Provisional Patent Application No. 62/866,582 filed Jun. 25, 2019 and European Patent Application No. 19201666.5 filed Oct. 7, 2019.

TECHNICAL FIELD

The present disclosure generally relates to a system comprising a monitoring device and a medicament delivery device. In particular, it relates to a system for monitoring the self-delivery of medicines and to a self-medicament delivery device incorporating such a monitoring device.

BACKGROUND

Medicament delivery devices such as pen injectors, auto-injectors and inhalers among others are generally known for the self-administration of a medicament by patients without the need for formal medical training. As just one example, patients suffering from diabetes may require repeated injections of insulin. Other patients may require regular injections of other types of medicaments, such as a growth hormone. Reusable medicament delivery devices are commonly used for those patients who are required to apply repeated doses.

There is an ever-increasing demand for monitoring the handling of medicament delivery devices. One important reason for monitoring the handling is to provide the user with information and alerts as to when the next dose delivery is scheduled, based on previous dose deliveries and based on prescribed medication schedules.

Some medicament delivery devices are provided with monitoring units integrated into the medicament delivery device. This has a number of drawbacks. One is that the medicament delivery device becomes rather complicated and expensive to manufacture. This is especially a problem if the medicament delivery device is a disposable device that is to be discarded or recycled after use. Another drawback is that it is not a simple task to modify a medicament delivery device that already is on the market by integrating monitoring functionality, because such modifications require new approvals from national health and/or regulatory authorities before they can be marketed.

An alternative is to provide monitoring units that can be releasably connected to a medicament delivery device. This solution has a number of advantages. First, the monitoring unit may be used many times which is an advantage when disposable medicament delivery devices are used. It is then easy to remove the monitoring unit from a used medicament delivery device that is to be discarded and to connect it to a new medicament delivery device for the subsequent dose delivery. Moreover, the monitoring units may be easily adapted or modified to be connected to medicament delivery devices on the market without the medicament delivery devices being affected regarding design and function by the monitoring units, thereby omitting any intervention by the national health and/or regulatory authorities.

WO2017/050781 A1 discloses a supplementary device that can be releasably attached to a medicament delivery device, with a non-contact sensor which may be a Hall sensor to detect to a position of a magnet arranged on the distal end of the plunger; therefore, the ejection process, especially the post-ejection state is detected by the supplementary device.

Detecting the ejection process through the position of the plunger is an accurate way for determining the injection process and the post-injection state; however, using the Hall sensor requires modifying the plunger with a magnet component in or on the plunger, which increases the cost of manufacture, since the plunger is usually made from plastic material. Additionally, without proper coating process, the magnet may interfere with some of the medicament, which again increases the cost and the complexity of the manufacture. Adding one or more magnets to the plunger rod may also increase the risk of interference with the plunger, which may cause a problem of potential dose accuracy.

SUMMARY

An object of the present disclosure is to provide an activation mechanism for an automatic medicament delivery device which solves problems of the prior art.

In the present disclosure, when the term "distal" is used, this refers to the direction pointing away from the dose delivery site. When the term "distal part/end" is used, this refers to the part/end of the delivery device, or the parts/ends of the members thereof, which under use of the medicament delivery device is/are located furthest away from the dose delivery site. Correspondingly, when the term "proximal" is used, this refers to the direction pointing to the dose delivery site. When the term "proximal part/end" is used, this refers to the part/end of the delivery device, or the parts/ends of the members thereof, which under use of the medicament delivery device is/are located closest to the dose delivery site.

An objective of this disclosure is to provide a simple and reliable way of detecting a medicament delivery process, such as at least one of the priming operation, the delivery start point, the delivery operation and/or the end of delivery of a self-medicament delivery device through a monitoring device which is releasably attached to the self-medicament delivery device. The object of this disclosure may be employed for monitoring the use or handling of fixed dose medicament delivery devices including single-dose medicament delivery devices such as auto-injectors, inhalers or multi-dose medicament delivery devices.

According to an aspect of the invention, the object is achieved by a medicament delivery device as described below.

There is hence provided a system comprising a monitoring device and a medicament delivery device wherein the monitoring device is configured to be releasably connected to the medicament delivery device and wherein the monitoring device comprises an induction sensor configured to detect a state of an electrically conductive drive member of the medicament delivery device in an medicament delivery process through an electrical current which is generated by a magnet field by the induction sensor on the electrically conductive drive element.

According to one embodiment the induction sensor comprises an inductor coil; wherein the state of the electrically conductive drive member is detected through a change of impedance in the inductor coil generated by the inductor coil's electrical current.

According to one embodiment the induction sensor comprises a first inductor coil and a second inductor coil; wherein the electrical current is induced on the second inductor coil from said first coil.

According to one embodiment the monitoring device further comprises one of a sound detector or a vibration detector.

According to one embodiment the monitoring device further comprises an accelerometer configured to detect the vibration or click sound of the medicament delivery device.

According to one embodiment the sound detector can be a microphone, resonant sensor or any other acoustic sensor.

According to one embodiment the vibration detector can be a resonant sensor, acoustic sensor, piezo-electronic sensor or any other vibration sensor.

According to one embodiment the detector is configured to detect a state of the medicament delivery device in a medicament delivery process.

According to one embodiment the monitoring device further comprises a computing element capable of correlating the information from the induction sensor with the information from the detector when the state of said electrically conductive drive element is changed.

According to one embodiment the computing element comprises a processor, a memory and a communication unit.

According to one embodiment the communication unit can be a short-range communication unit, such like RFID, NFC, infra-red, ZigBee, Bluetooth.

According to one embodiment the communication unit can be a long-range communication unit, such like 3G, 4G, CAT-M1, NB-IoT, LoRa, Sigfox, 5G, GPRS.

According to one embodiment the communication unit can provide a wireless or wired communication.

According to one embodiment, the processor and the memory are configured to process the information detected by the induction sensor and the detector and generate output data.

According to one embodiment the communication unit is configured to send an information related to the process of delivery based on output data to a remote computing device.

According to one embodiment the communication unit is configured to send a computer-readable instruction based on the process of delivery based on output data to a remote computing device.

According to one embodiment the remote computing device can be a personal computer, a cloud server, mobile phone or any other smart device with a communication model and a processor.

According to one embodiment the monitoring device might further comprises a display and/or an indication element, configured to provide an indication or an instruction to a user.

According to one embodiment the electrically conductive drive element is a coil spring configured to change state from a compressed state to a relaxed state.

According to one embodiment the electrically conductive drive element is a plunger rod configured to change state from a start state to a final state.

According to one embodiment the induction sensor is configured to detect the state of the compression spring through the difference of the density of spring coils.

According to one embodiment the induction sensor is configured to detect the absence or presence of the compression spring in a sensing area.

According to one embodiment the induction sensor is configured to detect the absence or presence of the plunger rod in a sensing area.

According to one embodiment the induction sensor further comprises a second inductor coil, configured to induce a current by the first inductor coil under the mutual inductance effect.

According to one embodiment the induction sensor further comprises a second inductor coil, configured to induce a current by another inductor coil arranged on the induction sensor under the mutual inductance effect.

According to one embodiment the medicament delivery device can be an injection device, an infusion device, an on-body device, an inhalation device or a medical sprayer.

According to one embodiment the medicament delivery device can be a disposable device or a reusable device.

According to one embodiment the medicament delivery device can be a non-selectable fixed dose device or a selectable variable dose device.

Other aspects, features, and advantages will be apparent from the summary above, as well as from the description that follows, including the figures and the claims.

Generally, all terms used in the claims are to be interpreted according to their ordinary meaning in the technical field, unless explicitly defined otherwise herein. All references to "a/an/the element, apparatus, component, means, etc. are to be interpreted openly as referring to at least one instance of the element, apparatus, component, means, etc.", unless explicitly stated otherwise.

BRIEF DESCRIPTION OF THE DRAWINGS

The specific embodiments of the concept of this disclosure will now be described, by way of example, with reference to the accompanying drawings, in which.

DETAILED DESCRIPTION

The present disclosure will now be described more fully hereinafter with reference to the accompanying drawings, in which exemplifying embodiments are shown. The concept of this disclosure may, however, be embodied in many different forms and should not be construed as limited to the embodiments set forth herein; rather, these embodiments are provided by way of example so that this disclosure will be thorough and complete, and will fully convey the scope of this disclosure to those skilled in the art. Like numbers refer to like elements throughout the description.

Figure 1B:
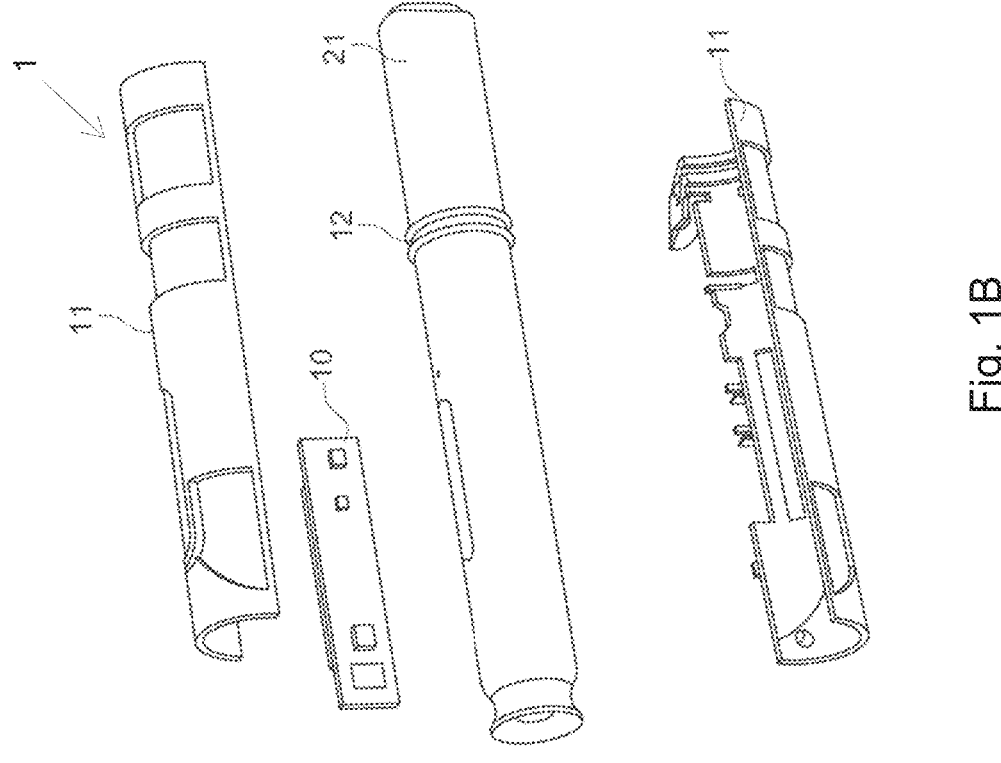
FIG. 1b displays an exploded view of the monitoring device.
Figure 1A:
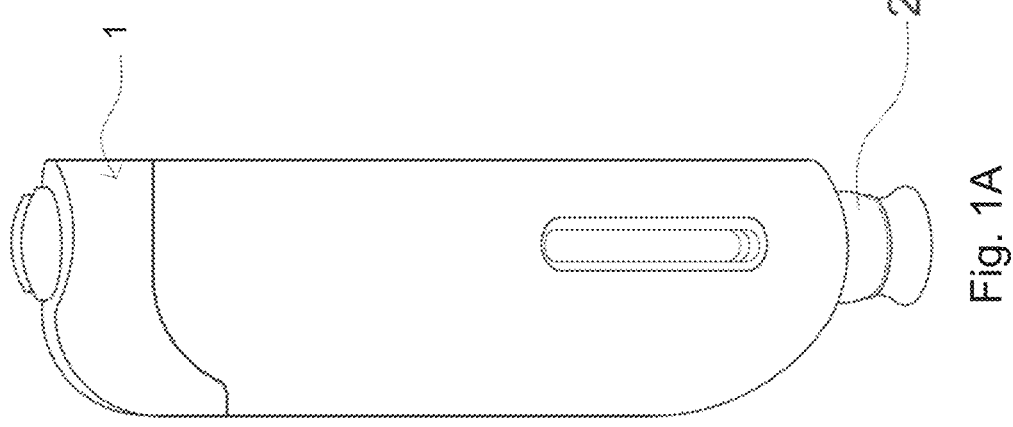
FIG. 1a displays a system comprises a monitoring device and a medicament delivery device.

FIG. 1a-1b generally illustrates a first embodiment of the system which comprises a monitoring device (1) and a medicament delivery device (2). The monitoring device (1) comprises a sleeve (11) defining a cavity for receiving the medicament delivery device (2); an attachment assembly (not show) configured to releasably hold the medicament delivery device in a specific position in relation to the sleeve (11). The attachment assembly can be of any type of releasable attachment assembly known for a person skilled in the art, e.g. cramping by a c-shape ring or cramping by a hinge connected hooking arm.

Figures 2A, 2B:
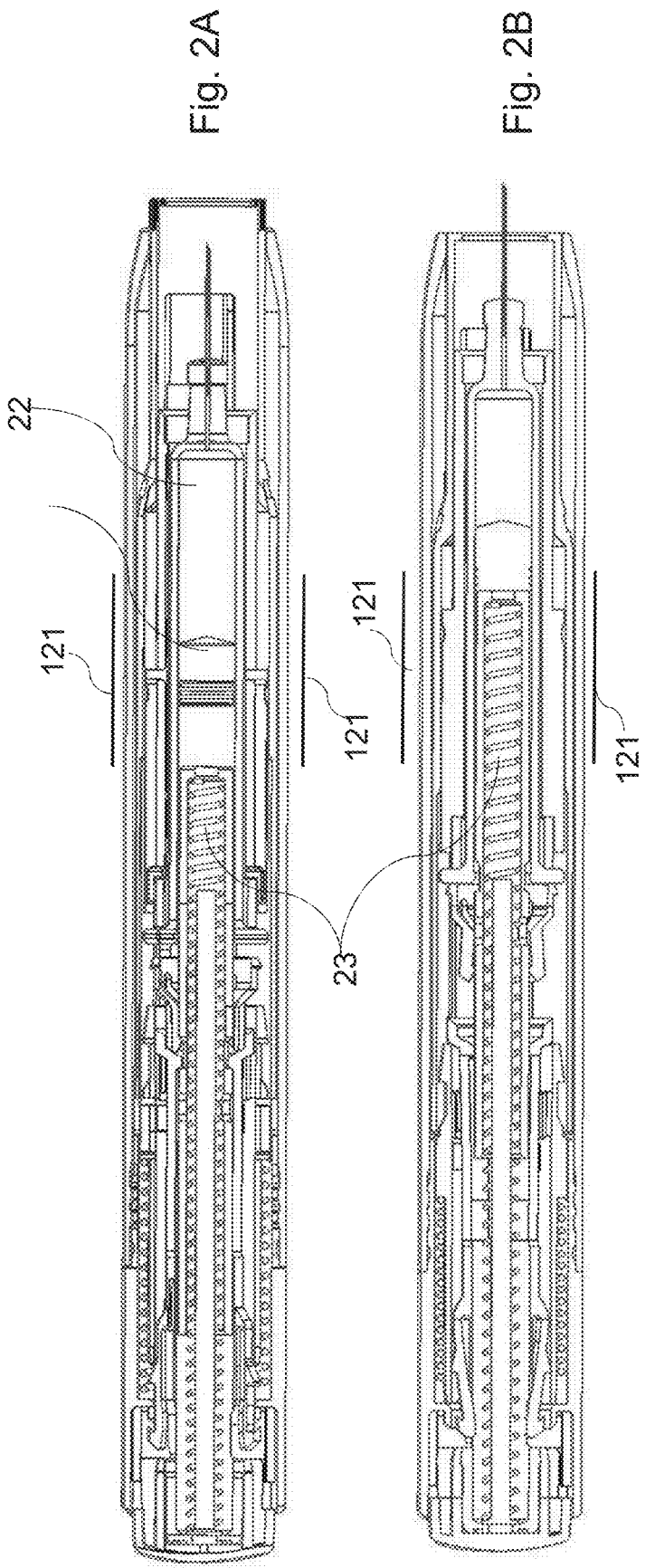
FIGS. 2a and 2b display a perspective cross-sectional longitudinal view of a first embodiment of the system.
Figures 3A, 3B:
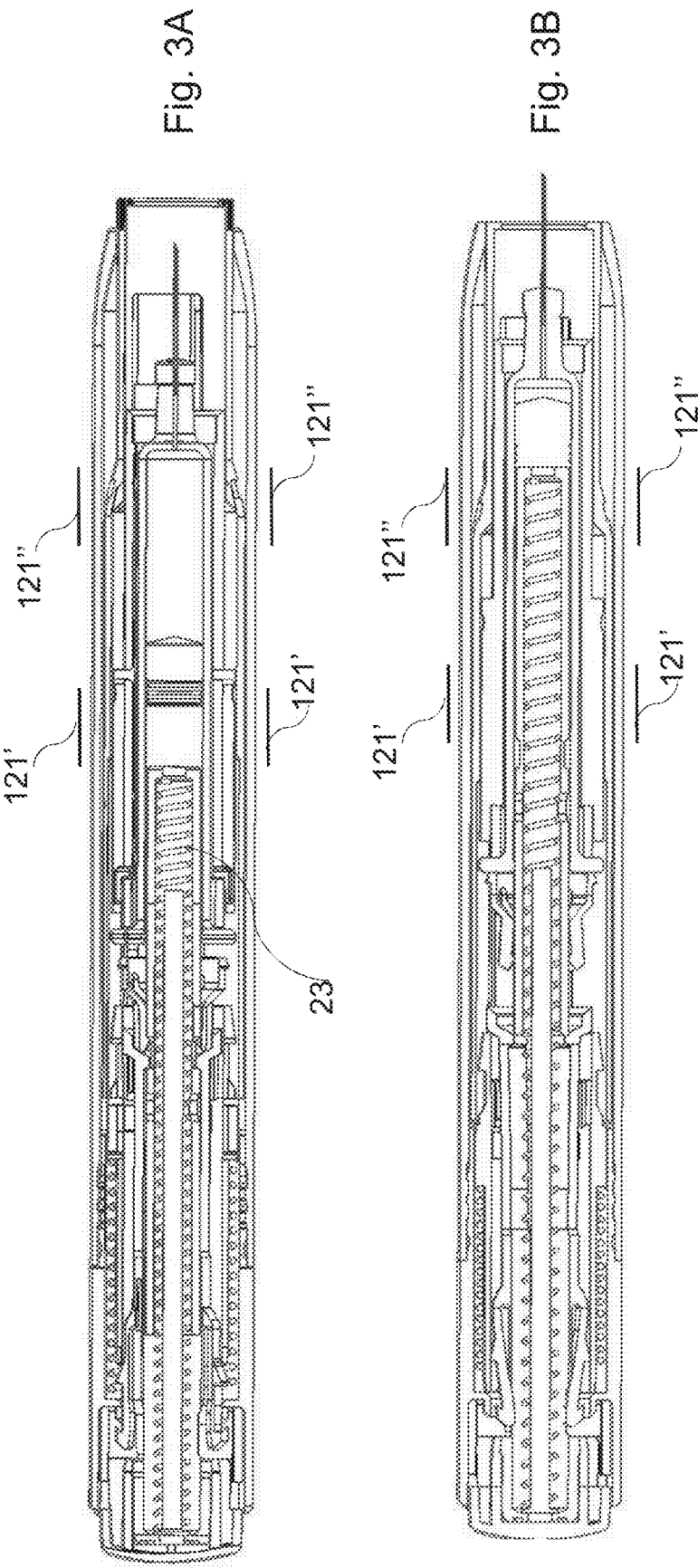
FIGS. 3a and 3b display a perspective cross-sectional longitudinal view of a second embodiment of the system.

The monitoring device further comprises a computing element (10) embedded on a print-circuit board (PCB) with at least a processor, a memory and a communication unit; a battery and an induction sensor (12). The induction sensor (12) is a circuit with at least one inductor coil. In a first embodiment of the system as shown in FIGS. 2a-b the circuit comprises one inductor coil (121). In a second embodiment of the system as shown in FIGS. 3*a-b* the circuit comprises a pair of inductor coils (121', 121"). The circuit is powered by the battery.

The medicament delivery device (2) comprises a body (21) receiving a medicament container (22). The medicament container (22) comprises a compartment that encloses a medicament therein and is sealed by a stopper. The medicament delivery device (2) further comprises a drive element (23), e.g. a power spring, configured to bias the stopper during a medicament delivery process, such like, at least one of the priming operation, the delivery start point, the delivery operation and the end of delivery; so that the medicament is ejected. The drive element (23) comprises at least an initial or compressed state and a final or relaxed state.

The delivery process of the medicament delivery device (2) is monitored by the induction sensor (12). The induction sensor (12) is arranged to detect a displacement from initial or compressed state to the final or relaxed state when the medicament delivery device (2) is attached to the monitoring device i.e. the system is in the attached state. The induction sensor can also be arranged to detect the absence or presence in the final state of the drive element (23) when the medicament delivery device (2) is attached to the monitoring device i.e. the system is in the attached state.

FIGS. 2*a-b* illustrate the first embodiment of the system in which the induction sensor (12) comprises a circuit with induction coil (121) and the drive element (23) is an electrically conductive component at least partially made of electrically conductive material permitting the flow of alternating currents (AC) that produce an alternating magnetic field of sufficient intensity to be detected by the induction coil in a specific position.

In the attached state, the medicament delivery device (2) is received in the cavity of the sleeve (11) in a specific position, such that the inductor coil (121) defines a central cavity which is at least partially wrapping and aligned with the medicament delivery container, and the drive element (23) is distally positioned in relation to central cavity defined by the inductor coil (121.)

FIG. 2*b* illustrates that during medicament delivery, the drive element (23) is moved forward to eject the medicament. The drive element (23) is therefore moved into the central cavity defined by the inductor coil (121). The movement of the drive element (23) from the initial or compressed state to the final or relax state causes changes of the metal density, from being fully compressed (high density) in the distal part of the device to being extended throughout the length of the device (low density).

To detect changes in metal density, the AC flowing in the inductor coil (121) will generate an alternating magnetic or electromagnetic field that will induce an eddy current on the drive element (23), and is relative to the quantity, distance, size, and composition of metal within the vicinity of the induction coil, which will change with the changing density of the spring. This eddy current generates its own opposing magnetic field (opposing the original field generated by the inductor coil) relative to the metallic object's conductivity, causing a change in the impedance of the circuit of the induction sensor (12). By sensing this change in impedance, the current state of the drive element (23) is detected, so that different states of the medicament delivery process such like pre-delivery, priming, ejection of the medicament, or end of delivery can be thereby detected by the induction sensor (12) based on the changes of the metal density of the drive element (23).

Instead detecting the displacement of the drive element (23) i.e. changes of the metal density of the drive element (23), the absence or presence of the drive element (23) can also be detected. This alternative way of detection can be performed by rearranging the inductor coil (121) such that the central cavity defined by the inductor coil (121) defines a sensing area and the drive element (23) will only pass through the central cavity of the inductor coil (121) at the end of delivery i.e. when the drive element is in its final or relaxed state, so that the end of delivery of the medicament delivery device (2) is detected by the induction sensor (12) through detecting the absence or presence of the drive element (23) in the sensing area.

FIG. 3*a-b* illustrate the second embodiment of the system in which the induction sensor (12) comprises a set of at least two inductor coils (121', 121").

The induction sensor (12) in this second embodiment comprises a circuit with a first inductor coil (121') and a second inductor coil (121").

In the attached state, the medicament delivery device (2) is received in the cavity of the sleeve (11) in a specific position, such that: —the first inductor coil (121') defines a first central cavity which is at least partially wrapping and aligned with a distal portion of the medicament delivery container, —the second inductor coil (121") defines a second central cavity which is at least partially wrapping and aligned with a proximal portion of the medicament delivery container, and—the drive element (23) is distally positioned in relation to first central cavity defined by the first inductor coil (121'). The second inductor coil (121") is proximally and discretely arranged in relation to the first inductor coil (121') and the second central cavity defined by the second inductor coil forms a sensing area. The first coil (121') is powered by the battery once the monitoring device (1) is operated. Also in the attached state, the drive element (23) is distally arranged in relation to both first and second inductor coil.

FIG. 3*b* illustrates that during medicament delivery, the drive element (23) is moved forward to eject the medicament from the initial state to the final state. The drive element (23) is therefore moved into the first central cavity defined by the first inductor coil (121') and thereafter into the second central cavity defined by the second inductor coil (121").

Before the drive element is moved into the first central cavity, the mutual inductance between the first and the second inductor coils is nearly zero; on the other hand, when the drive element (23) is moved into both the first and the second cavity to its final state, i.e. at the end of delivery, the drive element (23) acts as an iron core and allows mutual inductance between the coils, so that the first inductor coil (121') will induce a current on the second inductor coil (121") and therefore, the appearance of the drive element (23) in the sensing area defined by the second cavity is detected by the induction sensor (12).

The pair of inductor coils arrangement used in the second embodiment can also be used in combination with the detection mechanism used in the first embodiment. In that case, the first inductor coil (121') can be used to detect the priming and/or the progress of the delivery through changes of the impedance of the circuit of the induction sensor dependent on changes of the density of the drive element (23) with the way disclosed in first embodiment; and the second inductor coil (121") can be used to detect the end of injection by detecting the appearance of the drive element (23) through the mutual inductance.

For the absence or presence detection by the mechanism described in either embodiments, the drive element (23) can also be a plunger rod of the medicament delivery device (2) which is made of an electrically conductive material. The plunger rod comprises an initial state in which the plunger rod is hold against a forward biasing force; and a final state in which the plunger rod is moved to its forward most position under a forward biasing force. That's especially important to use in a non-spring driven device or non-compression spring driven device, such like gas power medicament delivery device or the medicament delivery device with a torsion spring or a clock spring, which will not move in the proximal direction during delivery.

Further, for increasing the accuracy of the detection of the delivery process, a sound detector or a vibration detector can be used in the monitoring device. Since the induction sensor (12) and the detector are configured to detect different pattern of the medicament delivery device (2), the accuracy of the detection of the delivery process can be increased. The detector is configured to detect the state of the medicament delivery device (2) by detecting the vibration/click sound; which is a more dynamic method than detecting the state of the medicament delivery device occurred by the interaction of two components upon the occurrence; there is a risk of inaccuracy that when using the detector as the only one detection arrangement in the monitoring device (1), there might be the environment noise or the friction damage between two components after several times of usage, especially for a reusable medicament delivery device; on the other hand, the induction sensor (12) is configured to detect the state of the drive element (23); which is a more static method of identifying the state of the drive element (23) and calculating the state of the medicament delivery device (2) accordingly; the risk of inaccuracy of the induction sensor (12) as the only detection arrangement in the monitoring device (1) might be evident during a malfunction of the drive element (23). By using a second detector in conjunction with the induction sensor (12), the risk mentioned above can be avoided or mitigated.

Rather than the induction sensor (12) being configured to detect the state of the drive element (23), the detector may be configured to detect a state of the medicament delivery device (2), which is one of the specific states of the delivery process, such as at least one of the priming operations, the delivery start point, the delivery operation and the end of delivery; by detecting a mechanical click sound generated by the interaction of two components of the medicament delivery device (2); such as, the click sound generated by an action that the plunger rod hits the stopper or the spring hits the rear end of the medicament delivery device (2) under the reaction force. The detector can be an accelerometer or inertial measurement unit, which is able to detect the slight vibration and the vibration that is generated by a click sound; and used in conjunction with the induction sensor (12) in both embodiments. The accelerometer can be a 3-axis accelerometer, and/or a 3-axis gyroscope so that the unique characteristics of vibration or the click sound can be identified based on the direction, orientation, frequency and magnitude; therefore, environment noise can be attenuated.

After the medicament delivery device (2) is received into the sleeve (11), the accelerometer detects the beginning "click" to indicate the start of the attached stated. The accelerometer will then detect the second "click" to indicate start of delivery. The computing element (10) will correlate the information from the induction sensor (12) with the information from the accelerometer when the state of said electrically conductive drive element is changed, such as, said drive element (23) is in the end position, in order to register that a delivery event has occurred. So that, in the instance where the drive element (23) is a coil spring, spring jams or malfunctions of the medicament delivery device (2) can be detected if the second "click" is detected, but the end of injection is not detected by the induction sensor (12).

The detector can also be used to detect the end of delivery with the induction sensor, for increasing the accuracy of the detection of the end of delivery. In that case, the first "click" can be used to indicate the start of delivery and the second "click" can be used as the indication of the end of the delivery; and the information from the induction sensor (12) can be the "confirmation" of the injection process.

The detector might be also used to detect the dose setting in a variable dose medicament delivery device which is either a disposable medicament delivery device or a reusable medicament delivery device.

The delivery device can be an injector such as an auto-injector, an inhaler or an on-body device.

The present disclosure has mainly been described above with reference to a few examples. However, as is readily appreciated by a person skilled in the art, other embodiments than the ones disclosed above are equally possible within the scope of the present disclosure, as defined by the appended claims.

The invention claimed is:

1. A system comprising a monitoring device and a medicament delivery device wherein the monitoring device is configured to be releasably connected to the medicament delivery device, wherein the monitoring device comprises an elongated sleeve defining a cavity for the medicament delivery device, and wherein the monitoring device comprises an induction sensor configured to detect a state of an electrically conductive drive element of the medicament delivery device in a medicament delivery process through an electrical current which is generated by a magnet field by the induction sensor on the electrically conductive drive element, wherein the electrically conductive drive element is a hollow tubular plunger configured to change state from a start state to a final state that partially contains a coil spring that changes from a compressed state to a relaxed state and wherein the induction sensor is configured to detect the absence or presence of the electrically conductive drive element in a sensing area.

2. The system according to claim 1, wherein the induction sensor comprises an inductor coil; wherein the state of the electrically conductive drive element is detected through a change of impedance in the inductor coil generated by the inductor coil's electrical current.

3. The system according to claim 2 wherein the induction sensor further comprises a second inductor coil, configured to be induced with a current by the induction coil under the mutual inductance effect.

4. The system according to claim 1, wherein the induction sensor comprises a first inductor coil and a second inductor coil; wherein the electrical current is induced on the second inductor coil from the first inductor coil.

5. The system according to claim 1, wherein the monitoring device further comprises one of a sound detector or a vibration detector.

6. The system according to claim 5, wherein either of the sound detector or the vibration detector is configured to detect a state of the medicament delivery device in a medicament delivery process.

7. The system according to claim 5, wherein the monitoring device further comprises a computing element capable of correlating the information from the induction sensor with the information from the detector when the state of said electrically conductive drive element is changed.

8. The system according to claim 1, wherein the monitoring device further comprises an accelerometer or inertia measurement unit detector.

9. The system according to claim 1, wherein the induction sensor is configured to detect the state of the coil spring through the difference of the density of spring coils.

10. The system according to claim 1, wherein the medicament delivery device is an injector.

11. A medicament delivery system comprising:

an injection device comprising a hollow tubular plunger that is electrically conductive, partially contains a coil spring that changes from a compressed state to a relaxed state, and is biased in a start state and movable from the start state to a final state;

a monitoring device releasably connected to a housing of the injection device, wherein the monitoring device comprises an elongated sleeve defining a cavity for the medicament delivery device, and where the monitoring device comprises:

an induction sensor that detects movement of the hollow tubular plunger from the start state to the final state through an electrical current which is generated by a magnet field by the induction sensor, wherein the induction sensor detects an absence or presence of either the hollow tubular plunger or the coil spring in a sensing area as the hollow tubular plunger moves from the start state to the final state.

12. The system according to claim 11, wherein the induction sensor comprises a first inductor coil and a second inductor coil, where the electrical current is induced on the second inductor coil from the first inductor coil.

13. The system according to claim 11, wherein the monitoring device further comprises a sound detector, a vibration detector, an accelerometer or inertia measurement unit detector.

14. The system according to claim 11, wherein the induction sensor detects a density difference of coils of the coil spring.

* * * * *